US011324511B2

(12) United States Patent
Zein et al.

(10) Patent No.: US 11,324,511 B2
(45) Date of Patent: May 10, 2022

(54) TISSUE LIGATION DEVICES AND METHODS FOR LIGATING TISSUE

(71) Applicant: THE CLEVELAND CLINIC FOUNDATION, Cleveland, OH (US)

(72) Inventors: Nizar Zein, Beachwood, OH (US); Shengqiang Gao, Beachwood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 145 days.

(21) Appl. No.: 15/952,410

(22) Filed: Apr. 13, 2018

(65) Prior Publication Data

US 2018/0296220 A1    Oct. 18, 2018

Related U.S. Application Data

(60) Provisional application No. 62/485,014, filed on Apr. 13, 2017.

(51) Int. Cl.
*A61B 17/12* (2006.01)
*A61B 17/04* (2006.01)
(Continued)

(52) U.S. Cl.
CPC .... *A61B 17/12013* (2013.01); *A61B 17/0467* (2013.01); *A61B 2017/0034* (2013.01);
(Continued)

(58) Field of Classification Search
CPC .... A61B 17/12013; A61B 2017/00734; A61B 17/0467; A61B 2017/0034;
(Continued)

(56) References Cited

U.S. PATENT DOCUMENTS

| | | | |
|---|---|---|---|
| 5,417,697 A * | 5/1995 | Wilk | A61B 18/10 606/113 |
| 5,423,830 A | 6/1995 | Schneebaum et al. | |
| 5,897,487 A * | 4/1999 | Ouchi | A61B 17/12013 600/127 |
| 5,906,620 A | 5/1999 | Nakao et al. | |

(Continued)

FOREIGN PATENT DOCUMENTS

| | | |
|---|---|---|
| JP | H10286224 A | 10/1998 |
| WO | 2013/169856 A1 | 11/2013 |
| WO | 2018/057963 A1 | 3/2018 |

OTHER PUBLICATIONS

PCT International Search Report and Written Opinion for corresponding International Application Serial No. PCT/US2018/027441, dated Aug. 31, 2018, pp. 1-22.

*Primary Examiner* — Kelly J Bekker
*Assistant Examiner* — Andrew P. Restaino
(74) *Attorney, Agent, or Firm* — Tarolli, Sundheim, Covell & Tummino LLP

(57) ABSTRACT

Tissue ligation devices and methods are provides to mechanically strangulate abnormal or undesirable tissue. Tissue ligation devices include a catheter having an outer diameter smaller than the inner diameter of a standard endoscope channel such that the catheter can be inserted into the endoscope. Tissue ligation devices also include a ligation system with an expandable hood disposed located at the distal end of the catheter. A suture extends through a lumen of the catheter and has a distal loop portion exposed outside of the expandable hood.

14 Claims, 4 Drawing Sheets

(51) Int. Cl.
*A61B 17/00* (2006.01)
*A61B 17/30* (2006.01)

(52) U.S. Cl.
CPC ............... *A61B 2017/00557* (2013.01); *A61B 2017/00566* (2013.01); *A61B 2017/00734* (2013.01); *A61B 2017/00818* (2013.01); *A61B 2017/00862* (2013.01); *A61B 2017/00867* (2013.01); *A61B 2017/00902* (2013.01); *A61B 2017/306* (2013.01)

(58) Field of Classification Search
CPC ........... A61B 2017/00557; A61B 2017/00566; A61B 2017/00818; A61B 2017/00862; A61B 2017/00867; A61B 2017/00902; A61B 2017/306; A61B 17/12; A61B 17/12009; A61B 2017/12004; A61B 2017/12018; A61B 17/04; A61B 17/0469; A61B 17/0482; A61B 2017/0409; A61B 2017/0411; A61B 2017/2212; A61B 17/221
See application file for complete search history.

(56) References Cited

U.S. PATENT DOCUMENTS

| | | | |
|---|---|---|---|
| 7,635,372 B2 | 12/2009 | Hamilton | |
| 2003/0158563 A1* | 8/2003 | McClellan | A61B 17/12009 606/151 |
| 2008/0312664 A1* | 12/2008 | Bardsley | A61B 17/12009 606/142 |
| 2009/0024139 A1* | 1/2009 | Saleh | A61B 17/221 606/113 |
| 2009/0093809 A1 | 4/2009 | Anderson et al. | |
| 2011/0270295 A1* | 11/2011 | Litvack | A61B 17/34 606/192 |
| 2012/0059225 A1* | 3/2012 | Gostout | A61B 17/0218 600/204 |
| 2013/0225934 A1 | 8/2013 | Raybin et al. | |
| 2014/0180337 A1* | 6/2014 | Miraki | A61B 17/0467 606/232 |
| 2014/0200398 A1* | 7/2014 | Hawkins | A61B 17/0469 600/37 |
| 2015/0265281 A1* | 9/2015 | Hawkins | A61B 17/12172 606/142 |
| 2016/0249932 A1 | 9/2016 | Rogers et al. | |
| 2017/0007259 A1* | 1/2017 | Kimura | A61B 17/00 |
| 2017/0245866 A1* | 8/2017 | Kiser | A61B 17/1285 |

* cited by examiner

TISSUE LIGATION DEVICES AND METHODS FOR LIGATING TISSUE

RELATED APPLICATION

The present application claims priority to U.S. Provisional Application No. 62/485,014 filed on Apr. 13, 2017, which is incorporated by reference herein in its entirety.

TECHNICAL FIELD

The present disclosure relates to devices and methods for ligating and strangulating tissue in a patient.

BACKGROUND

Varices are abnormally dilated vessels most commonly detected in the distal esophagus or proximal stomach. Despite advances in therapy over the last decade, variceal hemorrhage is associated with a mortality of at least 20% at 6 weeks. Endoscopic therapies for varices aim to reduce variceal wall tension by obliterating the varix. The two principal methods for treating varices are endoscopic sclerotherapy (EST) and endoscopic band ligation (EBL). EBL obliterates varices by causing mechanical strangulation with elastic bands. In general, an endoscope loaded with an elastic band is inserted into the varix to be banded. The varix is suctioned into a plastic hollow cylinder or cap attached to the endoscope tip. The elastic band is slipped over the tissue, causing necrosis, ulceration and eventual sloughing of the varix.

Esophageal varices are often associated with portal hypertension. Portal hypertension is an increase in the pressure within the portal vein. The increase in pressure is generally caused by a blockage in the blood flow through the liver. Increased pressure in the portal vein causes large varices to develop across the esophagus and stomach to bypass the blockage.

The most common cause of portal hypertension is cirrhosis. It is estimated that there are over 630,000 individuals with liver cirrhosis in the United States. Additionally, at least 30,000 new cases of cirrhosis are diagnosed annually. Nearly 90% of patients with cirrhosis will develop esophageal varices during their lifetime and 30% of patients will have an episode of variceal bleeding. EBL is recommended for the prevention of bleeding particularly in those patients with medium or large size varices.

SUMMARY

The present disclosure relates to devices and methods for ligating tissue. In an embodiment, a tissue ligation device comprises a catheter having a distal end, a proximal end, and a lumen extending therebetween. The catheter has an outer diameter smaller than the inner diameter of a biopsy channel of an endoscope. The tissue ligation device also includes a ligation system comprising an expandable hood located at the distal end of the catheter and a suture extending through the lumen and having a distal loop portion exposed outside of the expandable hood. The tissue ligation device also includes a handle located at the proximal end of the catheter comprising a suction port in communication with a suction source in an operative configuration.

In another embodiment, a method of ligating tissue in a patient is provided. The method comprises inserting an endoscope having a channel into the patient and inserting a tissue ligation device into the channel. The tissue ligation device comprises a catheter having a distal end, a proximal end, and a lumen extending therebetween. The tissue ligation device also includes a ligation system comprising an expandable hood located at the distal end of the catheter and a suture extending through the lumen of the catheter. The suture has a distal loop portion exposed outside of the expandable hood and has a proximal portion with proximal ends. The method further comprises positioning the expandable hood and distal loop portion of the suture adjacent to the tissue and expanding the expandable hood. The method further includes suctioning the tissue into the hood. The method further comprises pulling the proximal ends of the suture to form a knot around the tissue to ligate the tissue.

DETAILED DESCRIPTION

The present disclosure relates to devices and methods for ligating tissue. As used herein with respect to a described element, the terms "a," "an," and "the" include at least one or more of the described element unless otherwise indicated. Further, the term "or" refers to "and/or" unless otherwise indicated. In addition, it will be understood that when an element is referred to as being "on," "attached" to, "connected" to, "coupled" with, "contacting," in "communication" with etc., another element, it can be directly on, attached to, connected to, coupled with, contacting, or in communication with the other element or intervening elements may also be present. In contrast, when an element is referred to as being, for example, "directly on," "directly attached" to, "directly connected" to, "directly coupled" with, "directly contacting," or in "direct communication" with another element, there are no intervening elements present. It will also be appreciated by those of skill in the art that references to an element that is disposed "adjacent" another element may have portions that overlap or underlie the adjacent element. The term "operative configuration" refers to the configuration of a tissue ligation device during use in a patient. A term "patient" refers to any mammal and is preferably a human being.

Figure 1:
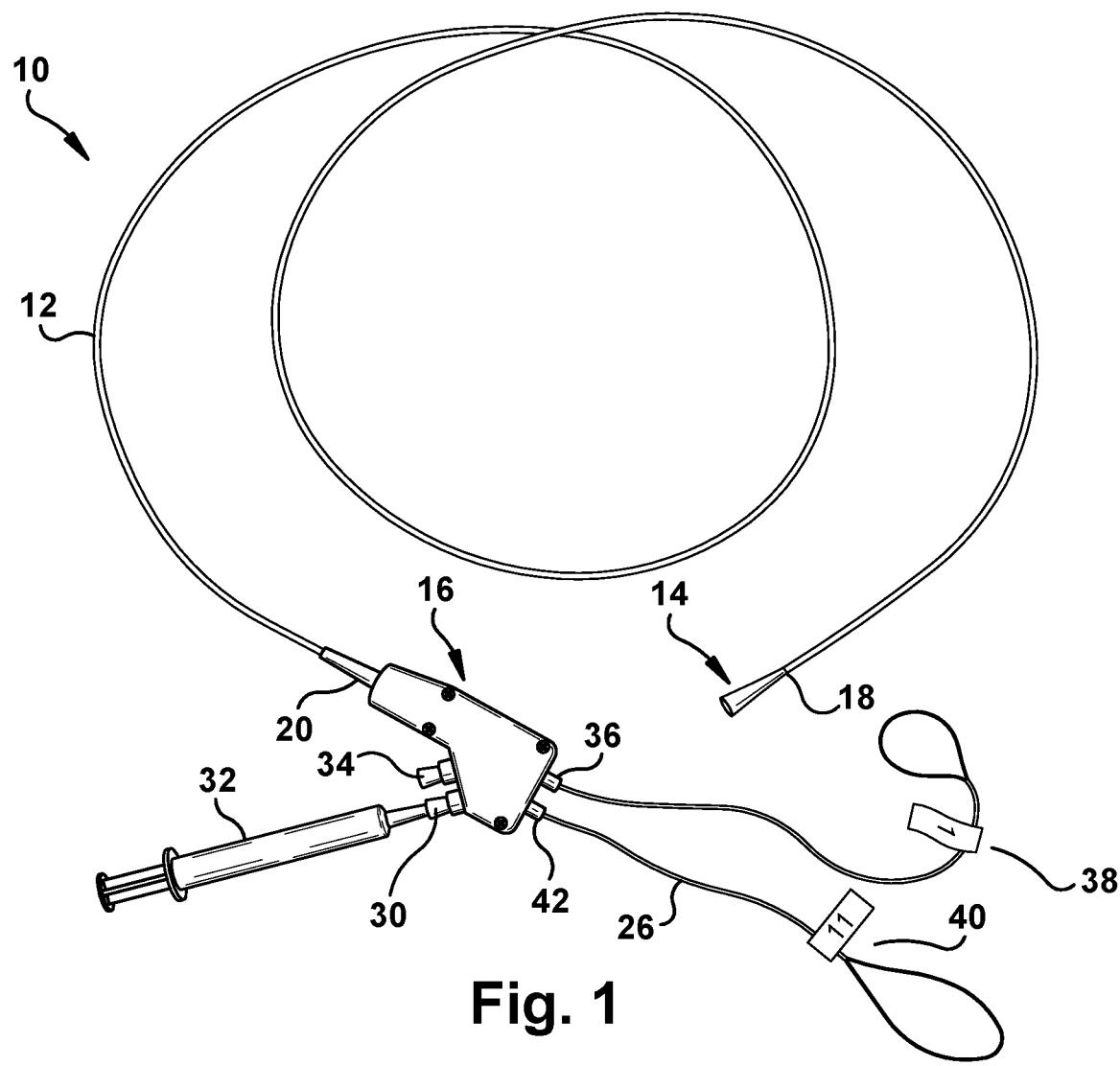
FIG. 1 is a top view of a tissue ligation device according to an embodiment of the present disclosure.
Figure 2:
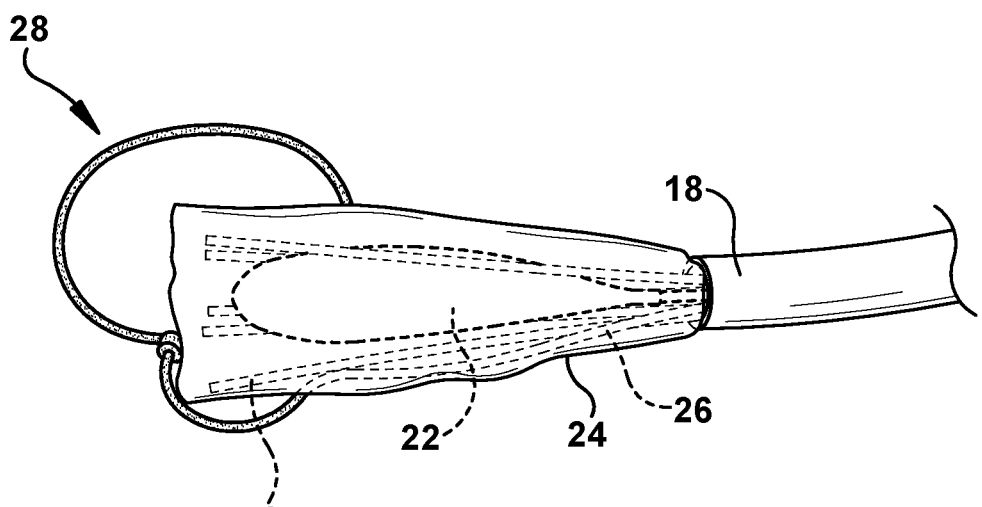
FIG. 2 is a side view of a distal portion of a tissue ligation device depicting components of a ligation system of the tissue ligation device according to an embodiment of the present disclosure.

Referring to FIGS. 1 and 2, in an embodiment, a tissue ligation device 10 comprises a catheter 12, a ligation system 14 and a handle 16. Catheter 12 has a distal end 18, a proximal end 20 and at least one lumen extending therebetween (not shown). Catheter 20 can also have a plurality of lumens including, for example, an inflation lumen in communication with an inflation source and sized to house an expandable member of ligation system 14 as described in more detail below; a suction lumen in communication with a suction source; and a suture lumen sized to receive a suture as described in more detail below. Catheter 12 has an outer diameter smaller than the inner diameter of a channel of an endoscope such as a biopsy channel. A standard endoscope has an inner diameter of between about 7.5 millimeters (mm) and 12.1 mm and the inner diameter of a standard biopsy channel is approximately 3.0 mm such as 2.8 mm.

Figure 3:
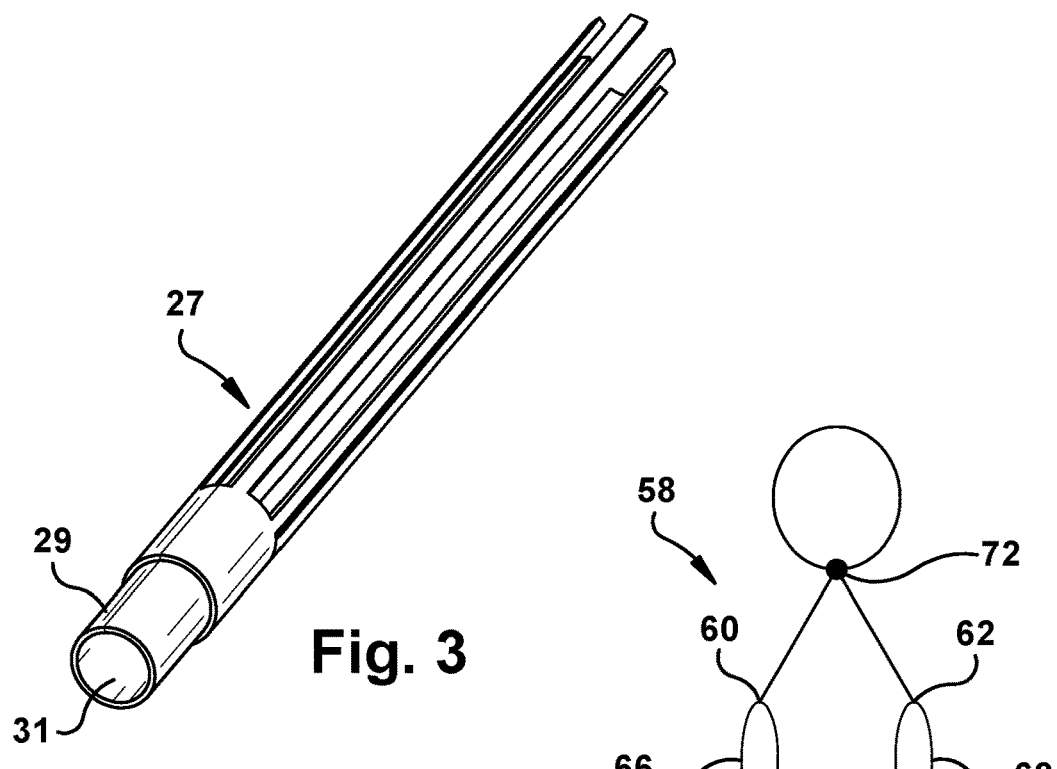
FIG. 3 is a side view of an expandable hood of a ligation system of a tissue ligation device according to an embodiment of the present disclosure.

Components of ligation system 14 are located at distal end 18 of catheter 12. As shown in FIG. 2, in certain embodiments, ligation system 14 can include an expandable member 22 located at distal end 18 of catheter 12, an expandable hood 24 disposed about expandable member 22 and also located at distal end 18 of catheter 12, and a suture 26 extending through a suture lumen of catheter 12. Suture 26 has a distal loop portion 28 exposed outside of expandable hood 24. For example, the distal portion of the suture can be looped around the expandable hood when the expandable hood is in a collapsed state. In certain embodiments, the distal loop is a clinch knot 72. Preferably, the suture is pre-loaded in the catheter. Referring to FIGS. 1 and 3, the suture can have a proximal portion 58 having a first end 60 and a second end 62. First end 60 can be releasably connected at a first connection point 66 to a distal end of a first filament 38 that has a proximal end that exits out of a first port of the handle and second end 62 can be releasably connected at a second connection point 68 to a distal end of a second filament 40 that has a proximal end that exits out of a second port of the handle (the connection points are enlarged for the sake of clarity). In certain embodiments, the first and second ends of the suture are connected to the connection points of the first and the second filament respectively via a heat sensitive material, such as, for example, epoxy, cyanoacrylate, polyurethane, etc. The proximal ends of the filaments can directly exit out of the ports of the handle or be connected to another filament or component that exits out the port to allow the operator to manipulate the suture. In certain embodiments, the first filament and the second filament are metallic wires operably coupled to a heat source. The heat source can be a battery 64, for example, housed in the handle.

In embodiments including an expandable member, the expandable member can include any suitable device that is capable of expanding or de-compressing and contracting or compressing. For example, the expandable member can be an inflatable balloon, a bladder, or an umbrella or parachute-like device. In the case of an expandable member that has a hollowed interior that accepts a material to inflate the expandable member, the expandable member can be inflated or diluted by delivering a fluid, air or other gas to the interior of the expandable member via an inflation lumen of the catheter.

In other embodiments, the ligation system does not include an expandable member but rather the expandable hood is self-expanding. For example, the expandable hood can comprise a flexible material such as a flexible plastic membrane including, for example, polyurethane, a polyether block amide, etc. The expandable hood also can be fabricated from a shape memory alloy. As shown in FIG. 3, expandable hood 27 has a distal end 29 defining a lumen 31 that has a smaller diameter than the rest of the expandable hood. Distal end 29 of expandable hood 27 can serve as a suction cup (as described in more detail below).

The expandable hood can include a frame comprising a plurality of struts 70 disposed about the inner or outer surface of the expandable hood to provide patency to the hood when expanded. The expandable hood can have any suitable shape that allows tissue to be suctioned into a cavity of the hood. For example, the expandable hood can be funnel-shaped. In certain embodiments, the hood is transparent.

Referring back to FIG. 1, handle 16 of tissue ligation device 10 is located at proximal end 20 of catheter 12. In embodiments including an expandable member, handle 16 includes an inflation port 30 in communication with an inflation source 32 at one end and an inflation lumen of catheter 12 at another end in an operative configuration. The inflation source can be, for example, an air, gas or fluid source. FIG. 1 depicts a syringe as inflation source 32 but other types of inflation sources can also be used. Inflation source can be any suitable device that causes the expandable member to expand or de-compress. Handle 16 can also includes a suction port 34 in communication with a suction source (not shown) in an operative configuration. The suction source can be any suitable device that can cause tissue to be suctioned into the hood of the ligation system. For example, suction source can be a syringe or vacuum. Handle 16 can also include a first port 36 and a second port 42 that are in communication with a suture lumen of catheter 12. As seen in FIG. 1, the proximal end of first filament 38 can extend out of port 36 and the proximal end of second filament 40 can extend out of second port 42.

Figure 5:
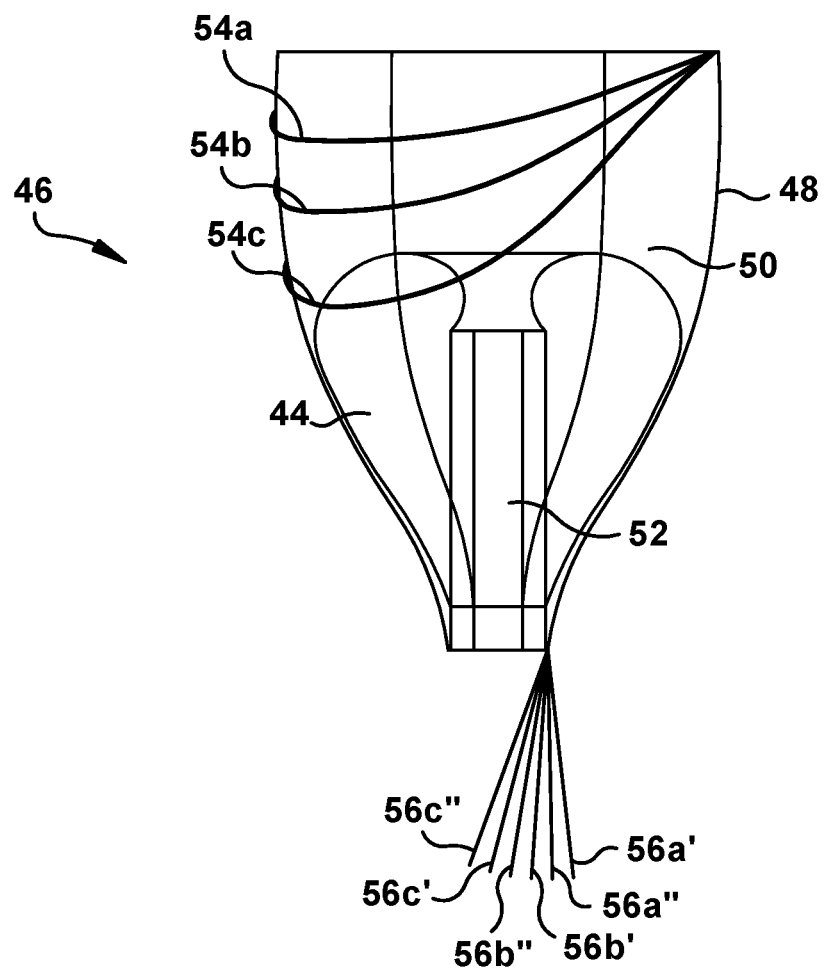
FIG. 5 is a side view of a distal end of a tissue ligation device depicting components of a ligation system of the tissue ligation device according to an embodiment of the present disclosure.
Figure 6:
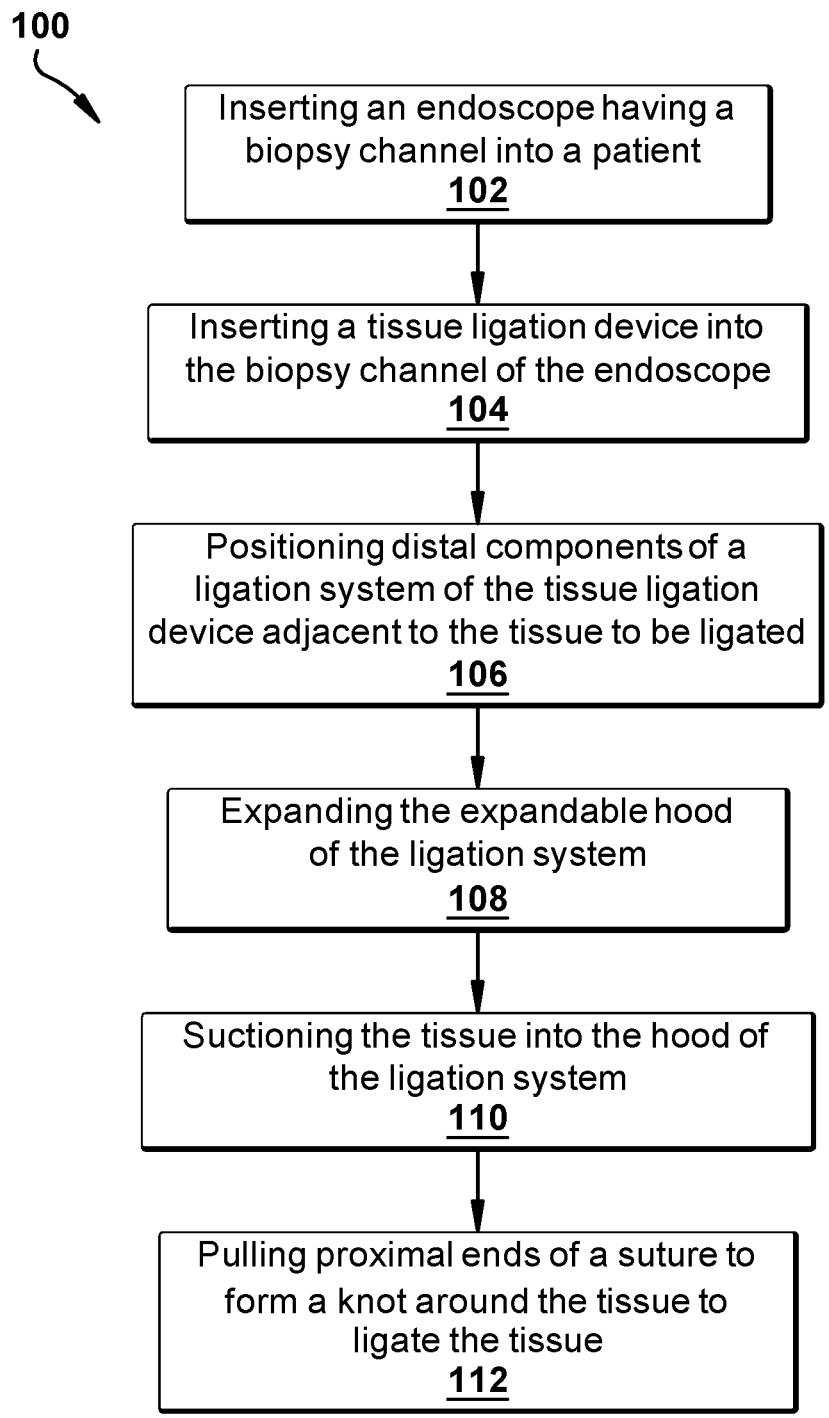
FIG. 6 is a flow chart outlining steps of a method of ligating tissue according to an embodiment of the present disclosure.

Referring to FIG. 5, the present disclosure also provides methods for ligating tissue in a patient. Method 100 can comprise inserting an endoscope into a patient 102. An endoscope generally includes a water tube, an air tube, a biopsy/suction channel, fiberoptic light guides, and a fiberoptic image bundle. The method can further include inserting a tissue ligation device into the biopsy channel of the endoscope 104. The tissue ligation device can include a catheter and a ligation system. The catheter can have a distal end, a proximal end, and a lumen extending therebetween. The ligation system can include an expandable hood located at the distal end of the catheter. The ligation system can also include a suture extending through the lumen of the catheter. The suture has a distal loop portion exposed outside of the collapsible hood and a proximal portion having proximal ends. After the tissue ligation device is inserted into the patient, the method further includes positioning distal components of the ligation system adjacent to the tissue to be ligated 106. In particular, the expandable hood and the distal loop portion of the suture are positioned adjacent to the tissue to be ligated. The method then comprises expanding the hood 108 and suctioning the tissue into the hood 110. The method further comprises pulling the proximal ends of a filament releasably connected to the suture to form a knot around the tissue to ligate the tissue 112. After the tissue has been ligated and strangulated, the suture can be severed. For example, filaments that are metallic wires that are connected to the proximal ends of the suture can be heated to sever the connection points between the metallic wires and the suture. Alternatively, a solvent can be delivered to the connection points to dissolve the connection points and therefore sever the proximal ends of the suture.

Figure 4:
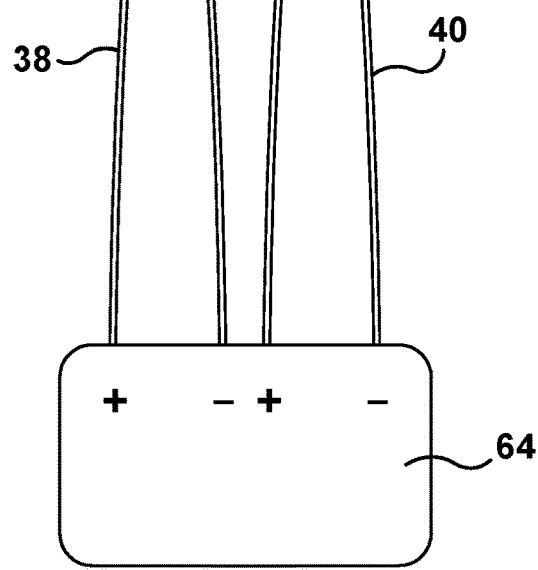
FIG. 4 is a schematic illustration of components of a tissue ligation device according to an embodiment of the present invention.

In an exemplary method and with reference to FIG. 4, a patient is intubated and a tissue ligation device is inserted through the endoscope channel. Once reaching the target tissue, an expandable member, such as a balloon 44, of a ligation system 46 is inflated. As a result, the hood 48 is opened up to 1.2 or 1.5 centimeter (cm) in diameter, for example. A cup 50 is formed by the combination of the inflated balloon 44 and the hood 48 as illustrated in FIG. 3.

A vacuum channel 52 is located inside cup 50 and one or more strangulation loops 54 of one or more sutures 56 are pre-loaded outside of cup 50 and are disposed on the outer surface of hood 48. The tissue to be ligated is then suctioned into cup 50. A proximal end of a filament connected to one distal end of suture 56 and exiting a port of the handle is pulled in the proximal direction. The knot can be locked or tightened by pulling a proximal end of another filament connected to another distal end of the suture 56 to create an improved clinch knot. After the tissue has been strangulated, the suture can be cut by a battery operated cutting mechanism. For example, a battery powered metal wire can generate heat at certain spots where the suture is being cut. The heat weakens and breaks the suture. The steps can be repeated to ligate more tissue.

Methods as disclosed herein can be used in conjunction with the administration of pharmaceutical or biological agents. For example, methods of treating varices can include administering pharmaceutical agents, such as beta blockers, or biological agents as adjunct therapy.

Methods and devices as described herein can be used to ligate abnormal or otherwise undesirable tissue. Such tissue can include a varix in a vein, artery or lymphatic vessel. Non-limiting examples include esophageal varices and gastric varices. Such varices are dilated blood vessels in the esophagus or stomach generally caused by portal hypertension and commonly stemming from cirrhosis of the liver. Methods and devices can also be used to ligate a hemorrhoid; a polyp; a cancerous lesion that can be removed, for example, by endoscopic mucosal resection; an arteriovenous malformation; a Mallory-Weiss tear; a Dieulofoy's lesion; a multifocal venous malformations resulting in, for example, blue rubber bleb nevus syndrome; or diverticula resulting in, for example, diverticular bleeding. Accordingly, methods and devices as disclosed herein can be used to treat esophageal variceal bleeding, prevent primary variceal bleeding in patients with varices, prevent re-bleeding after an initial variceal hemorrhage, and treat rectal hemorrhoids.

Methods and devices as disclosed herein have several advantages. The catheter of the tissue ligation device has an outer diameter smaller than the inner diameter of a standard endoscope. As such, the tissue ligation device provides a "through the scope" technique precluding the need for a second intubation needed for current tissue banding devices. This feature also shortens the procedure time and the sedation/anesthesia time since the procedure can be done in one step with a single esophageal intubation, for example. The tissue ligation device does not add to the existing outer diameter of standard endoscopes since no cap attachment (into which tissue is suctioned) is needed as with current devices. As such, children or small adults with limited oropharyngeal space can be intubated since there is no banding cap needed that increases the endoscope diameter. Further, the tissue ligation device provides a clinician with the ability to perform suctioning of the tissue away from the bodily lumen into which the tissue ligation device is inserted. For instance, a clinician can perform suctioning of a varix away from the wall of the esophagus thereby avoiding deep ulcerations often occurring in endoscopic sclerotherapy. In addition, the tissue ligation device can provide mechanical strangulation of tissue, such as a varix or mucosa, as opposed to injecting chemical agents such as sclerosing agents or adhesives into the bloodstream via the varix or the surrounding tissue thereby avoiding potential complications. A tissue ligation device as disclosed herein also provides an improved field of vision during the endoscopic procedure compared to existing band ligation devices where visibility is significantly limited due to the cylindrical cap that is needed and that is attached to the leading end of the endoscope.

Each of the disclosed aspects and embodiments of the present disclosure may be considered individually or in combination with other aspects, embodiments, and variations of the disclosure. Further, while certain features of embodiments of the present disclosure may be shown in only certain figures, such features can be incorporated into other embodiments shown in other figures while remaining within the scope of the present disclosure. In addition, unless otherwise specified, none of the steps of the methods of the present disclosure are confined to any particular order of performance. Furthermore, all references cited herein are incorporated by reference in their entirety.

What is claimed is:

1. A tissue ligation system comprising:
   a catheter having a distal end, a proximal end, and a lumen extending longitudinally therethrough, the catheter having an outer diameter configured to be less than an inner diameter of a biopsy channel of an endoscope, the inner diameter of the biopsy channel being approximately 3.0 millimeters;
   a frame comprising a plurality of circumferentially disposed struts and having a distal portion, a proximal portion, and a lumen extending therebetween, the proximal portion connected to the distal end of the catheter;
   a plurality of sutures extending through the catheter lumen, and having distal loop portions and proximal portions, the distal loop portions disposed on the distal portion of the frame and configured to form a knot and cinch and tie off tissue, the proximal portions releasably connected to at least one filament; and
   a handle located at the proximal end of the catheter.

2. The tissue ligation system of claim 1, further comprising an expandable balloon disposed within the frame at the distal portion thereof.

3. The tissue ligation system of claim 1, wherein the at least one filament is a metallic wire and the handle comprises a heat source operably coupled to the metallic wire.

4. The tissue ligation system of claim 3, wherein the heat source is a battery.

5. The tissue ligation system of claim 1, wherein the proximal portions of the plurality of sutures are connected to the at least one filament via a heat sensitive material.

6. The tissue ligation system of claim 1, wherein the plurality of sutures are pre-loaded in the tissue ligation device.

7. A method of ligating tissue in a patient comprising:
   inserting an endoscope having a channel into the patient;
   inserting a tissue ligation device into the channel, the tissue ligation device comprising:
   a catheter having a distal end, a proximal end, and a lumen extending
   therebetween, the catheter having an outer diameter configured to be less than an inner diameter of the channel of the endoscope, the inner diameter of the channel being approximately 3.0 millimeters; and
   a ligation system comprising:
   a frame comprising a plurality of circumferentially disposed struts and having a distal portion, a proximal portion, and a lumen extending therebetween, the proximal portion connected to the distal end of the catheter
   a plurality of sutures extending through the lumen of the catheter, the plurality of sutures having distal loop portions disposed on the distal portion of the frame and configured to form a knot and cinch and tie off tissue and having proximal portions with proximal ends releasably connected to at least one filament;

positioning the frame and the distal loop portions of the plurality of sutures adjacent to the tissue; and pulling the proximal ends of the plurality of sutures to form a knot around the tissue to cinch and tie off the tissue.

8. The method of claim 7, wherein the proximal ends of the plurality of sutures are connected to the at least one-filament at a connection point.

9. The method of claim 8, wherein the at least one filament is a metallic wire operably coupled to a heat source.

10. The method of claim 9, further comprising activating the heat source to generate heat in the metallic wire, and transferring the heat to the connection point to sever the proximal ends of the plurality of sutures from the metallic wire.

11. The method of claim 8, further comprising delivering a solvent to the connection point to sever the proximal ends of the plurality of sutures from the connection point.

12. The method of claim 7, wherein the proximal ends of each of the plurality of sutures comprise a first proximal end and a second proximal end.

13. The method of claim 12, further comprising pulling the first proximal end of each of the plurality of sutures so that the each of the distal loop portion engages the tissue and then pulling the second proximal end of each of the plurality of sutures to cinch the plurality of sutures to form a locked clinch knot.

14. The method of claim 7, wherein the tissue is a varix, a hemorrhoid, a polyp, a cancerous lesion, an arteriovenous malformation, a Mallory-Weiss tear, a Dieulofoy's lesion, multifocal venous malformations resulting in blue rubber bleb nevus syndrome, diverticula, a combination thereof.

* * * * *